United States Patent [19]

Penco et al.

[11] Patent Number: 4,604,381
[45] Date of Patent: Aug. 5, 1986

[54] 4-DEMETHOXY-13-DIHYDRODAUNORUBICIN AND USE THEREOF

[75] Inventors: Sergio Penco, Milan; Federico Arcamone, Nerviano; Anna Maria Casazza, Milan, all of Italy

[73] Assignee: Farmitalia Carlo Erba S.p.A., Milan, Italy

[21] Appl. No.: 668,178

[22] Filed: Nov. 5, 1984

Related U.S. Application Data

[63] Continuation of Ser. No. 398,987, Jul. 16, 1982, abandoned.

[51] Int. Cl.4 ............... A61K 31/71; C07H 15/24
[52] U.S. Cl. .................................. 514/34; 336/6.4
[58] Field of Search ................ 536/6.4; 424/180; 514/34

[56] References Cited

U.S. PATENT DOCUMENTS 4,046,878  9/1977  Patelli et al. ............... 536/6.4
4,146,616  3/1979  Penco et al. ................ 536/6.4
4,267,312  5/1981  Oki et al. .................... 536/6.4

OTHER PUBLICATIONS

Pigman, *The Carbohydrates*, 1957, p. 107.

Primary Examiner—Johnnie R. Brown
Assistant Examiner—Elli Peselev
Attorney, Agent, or Firm—Sheldon Palmer

[57] ABSTRACT

A new antitumor anthracycline glycoside, 4-demethoxy-13-dihydrodaunorubicin, is disclosed.

The new compound is prepared by reduction of the side-chain ketone function of the known 4-demethoxydaunorubicin, with sodium borohydride in aqueous solution at room temperature.

3 Claims, No Drawings

4-DEMETHOXY-13-DIHYDRODAUNORUBICIN AND USE THEREOF

This application is a continuation of application Ser. No. 398,987 filed July 16, 1982, abandoned.

The invention relates to an antitumor antibiotic of the anthracycline glycoside series, a process for its preparation, pharmaceutical compositions containing it and its use. In one aspect thereof, the invention provides 4-demethoxy-13-dihydrodaunorubicin, which has the formula

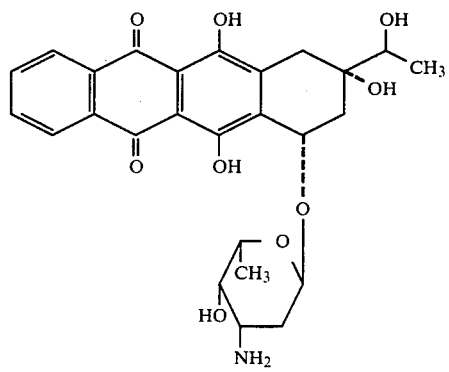

and its pharmaceutically acceptable acid addition salts.

In another aspect thereof, the invention provides a process for preparing 4-demethoxy-13-dihydrodaunorubicin.

The compound according to the invention may be prepared by reducing the side-chain ketone function of 4-demethoxydaunorubicin, a compound described and claimed in U.S. Pat. No. 4,046,878, owned by the unrecorded assignee hereof. The treatment of 4-demethoxydaunorubicin with an excess of sodium borohydride gives 4-demethoxy-13-dihydrodaunorubicin in high yield. The sodium borohydride may be added to an aqueous solution of 4-demethoxydaunorubicin at room temperature at pH 10. The reduction is very fast. After removal of the excess reducing agent, the crude product, obtained by extraction with organic solvents from the aqueous phase, may be purified by chromatography and isolated, preferably as one of its salts, for example the hydrochloride. This process is within the scope of the invention.

The invention further provides a pharmaceutical composition comprising 4-demethoxy-13-dihydrodaunorubicin or a pharmaceutically acceptable salt thereof in admixture with a diluent or carrier therefor.

The invention is illustrated by the following Example.

EXAMPLE

Preparation of 4-demethoxy-13-dihydrodaunorubicin

A solution of 0.875 g of 4-demethoxydaunorubicin in 250 ml of water was adjusted to pH 10 with 0.1N aqueous solution of sodium hydroxide and treated with 0.09 g of sodium boro hydride. After 8 to 10 minutes the solution was poured under stirring into 250 ml of 0.2N aqueous hydrochloric acid. Then the solution, adjusted to pH 8.5, was repeatedly extracted with ethyl acetate. The combined extracts were evaporated to dryness under vacuum. The residue, dissolved in methylene dichloride, was purified by chromatography on a column of silica gel using, as eluent, a mixture of methylene dichloride:methanol:water (100:20:2 by volume). The fractions containing the title compound were collected and evaporated to a small volume.

Upon addition of the stoichiometric amount of 0.1N methanolic hydrogen chloride and excess diethyl ether to the solution a precipitate was obtained. The product was collected, washed with ether and dried under vacuum. 0.5 g of the title compound was obtained: m.p. 159°–160° (dec.), FD-MS: m/z (M+.); TLC on Kieselgel plates (Merck F$_{254}$) solvent system chloroform:methanol:acetic acid:water (8:2:0.7:0.3 by volume): Rf 0.26. "E. Merck" is a Trade Marck.

BIOLOGICAL ACTIVITY

ACTIVITY IN VITRO

Cytotoxicity. Colony inhibition test on HeLa cells.

The test was carried on HeLa according to the method described in J. Med. Chem., 1975, 18, 703. Exponentially growing cells (2 days after inoculation) were treated with several concentrations of daunorubicin, 4-demethoxydaunorubicin, and 4-demethoxy-13-dihydrodaunorubicin.

After 24 hours of exposure to the drugs, the cells were washed, trypsinized and plated (200 cells/plate). On day 6 the colonies containing more than 50 cells were counted. The dose causing 50% inhibition was calculated on the basis of dose-reponsive curves. The data are reported in Table 1.

TABLE 1

| Colony inhibition on HeLa cells[a] | | | |
|---|---|---|---|
| Compound | Dose (ng/ml) | % Colonies[b] | DI$_{50}$ (ng/ml) |
| Daunorubicin | 25 | 3 | |
| | 12.5 | 32 | 11 |
| | 6.2 | 92 | |
| 4-demethoxy daunorubicin | 25 | 0 | |
| | 12.5 | 10 | |
| | 6.2 | 37 | 5.5 |
| | 3.1 | 73 | |
| | 1.5 | 126 | |
| 4-demethoxy-13-dihydrodaunorubicin | 12.5 | 0 | |
| | 6.2 | 9 | 3 |
| | 3.1 | 45 | |
| | 1.56 | 100 | |

[a] 24 hours exposure
[b] % respect with control

ANTITUMOR ACTIVITY IN VIVO

Activity against ascitic leukemia P 388

The experiments were performed on CDF-1 mice inoculated i.p. with 10$^6$ leukemic cells/mouse.

TABLE 2

| Activity against leukemia P 388: treatment i.p. on day 1 | | | |
|---|---|---|---|
| Compound | dose (mg/kg) | T/C % | toxic deaths |
| daunorubicin | 4.4 | 180 | 0/10 |
| | 6.6 | 168 | 2/10 |
| 4-demethoxydaunorubicin | 0.33 | 150 | 0/10 |
| | 0.5 | 170 | 0/10 |
| | 0.75 | 155 | 3/10 |
| 4-demethoxy-13-dihydrodaunorubicin | 0.14 | 130 | 0/10 |
| | 0.22 | 160 | 0/10 |
| | 0.33 | 170 | 0/10 |
| | 0.5 | 170 | 3/10 |

Activity against Gross leukemia

The experiments were performed on C3H mice inoculated i.v. with $2 \times 10^6$ leukemic cells/mouse.

TABLE 3

Activity against Gross leukemia
i.v. treatment on day 1

| Compound | dose (mg/kg) | T/C % | toxic deaths |
| --- | --- | --- | --- |
| daunorubicin | 10 | 150 | 0/10 |
|  | 15 | 183 | 0/10 |
|  | 22.5 | 233 | 0/10 |
| 4-demethoxy-daunorubicin | 1.9 | 233 | 0/10 |
|  | 2.5 | 233 | 0/10 |
|  | 3.3 | 266 | 0/10 |
| 4-demethoxy-13-dihydrodaunorubicin | 0.84 | 200 | 0/10 |
|  | 1.26 | 250 | 0/10 |
|  | 1.9 | 258 | 0/10 |

TABLE 4

Activity against advanced mammary Carcinoma[a]
The experiments were performed on C3H female mice inoculated with $2 \times 10^6$ tumor cells/mouse

| Compounds | dose (mg/kg) | growth %[b] on day 48 | inhibition % on day 48 |
| --- | --- | --- | --- |
| Controls | — | 3476 |  |
| 4-demethoxydaunorubicin | 0.8 | 4322 | 0 |
|  | 1.2 | 2029 | 42 |
| 4-demethoxy-13-dihydrodaunorubicin | 0.6 | 5124 | 0 |
|  | 0.8 | 3374 | 3 |
|  | 1.2 | 1201 | 65 |

[a]treatment once a week × 4, starting when the tumor was palpable.

[b] $\left( \dfrac{\text{tumor weight at the end of treatment}}{\text{tumor weight at the beginning of treatment}} \times 100 \right) - 100$

What we claim is:
1. An anthracycline glycoside having the formula:

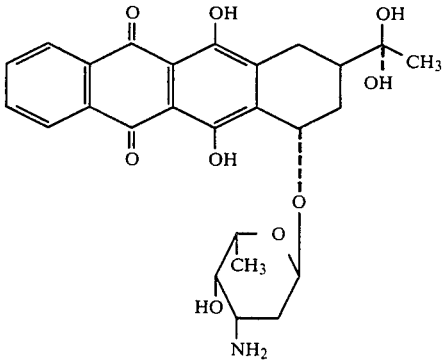

and its pharmaceutically acceptable acid addition salts.

2. A method of inhibiting the growth of a tumor selected from the group consisting of P 388 leukemia and Gross leukemia, said method comprising administering to a host afflicted therewith, a therapeutically effective amount of the anthracycline glycoside as claimed in claim 1.

3. A pharmaceutical composition for treating a tumor selected from the group consisting of P388 leukemia and Gross leukemia, said composition comprising a therapeutically effective amount of the anthracycline glycoside as claimed in claim 1 in combination with an inert carrier therefor.

* * * * *